United States Patent [19]

Skeels et al.

[11] Patent Number: 5,095,169

[45] Date of Patent: Mar. 10, 1992

[54] NORMAL PARAFFIN HYDROCARBON ISOMERIZATION PROCESS USING ACTIVATED ZEOLITE BETA

[75] Inventors: Gary W. Skeels, Brewster; Edith M. Flanigen, White Plains, both of N.Y.

[73] Assignee: UOP, Des Plaines, Ill.

[21] Appl. No.: 596,157

[22] Filed: Oct. 11, 1990

Related U.S. Application Data

[60] Continuation-in-part of Ser. No. 366,263, Jun. 12, 1989, abandoned, which is a division of Ser. No. 175,332, Mar. 30, 1988, abandoned.

[51] Int. Cl.$^5$ ................................................. C07C 5/13
[52] U.S. Cl. ....................................................... 585/739
[58] Field of Search ............................................ 585/739

[56] References Cited

U.S. PATENT DOCUMENTS

| Re. 28,341 | 2/1975 | Wadlinger et al. | 208/120 |
|---|---|---|---|
| 3,150,205 | 9/1964 | Krane et al. | 260/683.65 |
| 3,308,069 | 3/1967 | Wadlinger et al. | 252/455 |
| 4,210,771 | 7/1980 | Holcombe | 585/701 |
| 4,428,819 | 1/1984 | Shu et al. | 585/737 |
| 4,501,926 | 2/1985 | La Pierre et al. | 585/739 |
| 4,518,485 | 5/1985 | LaPierre et al. | 208/89 |
| 4,554,065 | 11/1985 | Albinson et al. | 208/59 |
| 4,554,145 | 11/1985 | Rubin | 502/77 |
| 4,642,226 | 2/1987 | Calvert et al. | 423/328 |
| 4,647,368 | 3/1987 | McGuiness et al. | 208/60 |

FOREIGN PATENT DOCUMENTS 0159846 10/1985 European Pat. Off. .

*Primary Examiner*—Curtis R. Davis
*Attorney, Agent, or Firm*—Thomas K. McBride; John F. Spears, Jr.; Richard E. Conser

[57] ABSTRACT

The present invention relates to processes for isomerizing normal paraffin hydrocarbons to produce products containing non-normal hydrocarbons using a zeolite beta catalyst that has been activated in order to enhance its catalytic properties. In accordance with the present invention, the zeolite beta catalyst is activated at a temperature effective to substantially reduce the concentration of strong acid species, i.e., hydronium cations, without substantially reducing the concentration of weak acid species, i.e., hydroxoaluminum cations, both of said strong acid species and weak acid species being initially present on the catalyst prior to activation. In addition, the isomerization step is preferably conducted at a temperature at least 300° C. lower than the activation temperature. Additional treatment steps that are preferably performed prior to the activation step described above include a calcining step wherein a synthesized zeolite beta catalyst containing a templating agent is calcined at a temperature in the range of from about 200° to 1000° C. in order to remove a substantial portion of the catalyst templating agent and an ion-exchanging step wherein the calcined catalyst is ion-exchanged with a salt solution containing at least one hydrogen forming cation selected from $NH_4^+$ and quaternary ammonium.

22 Claims, 3 Drawing Sheets

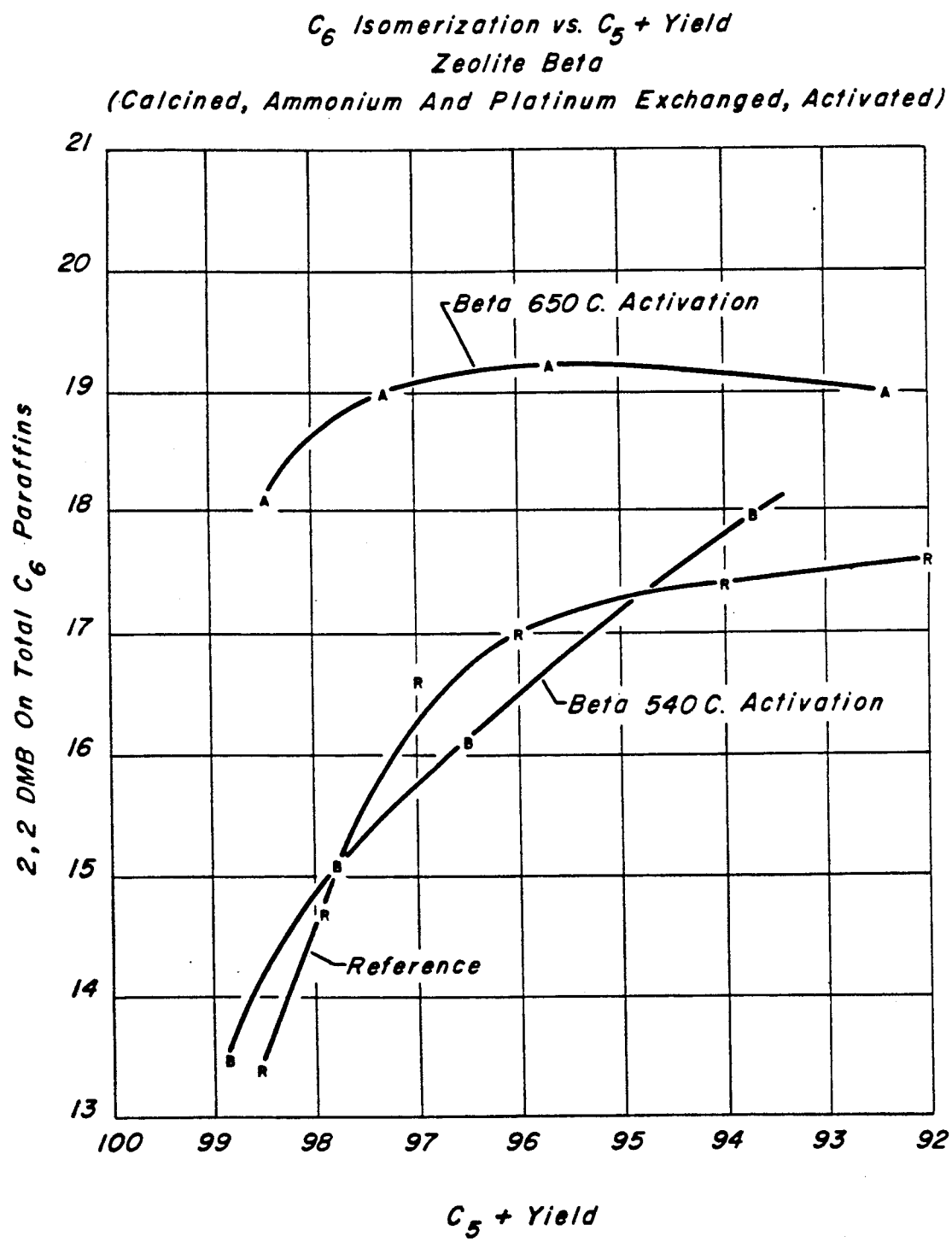

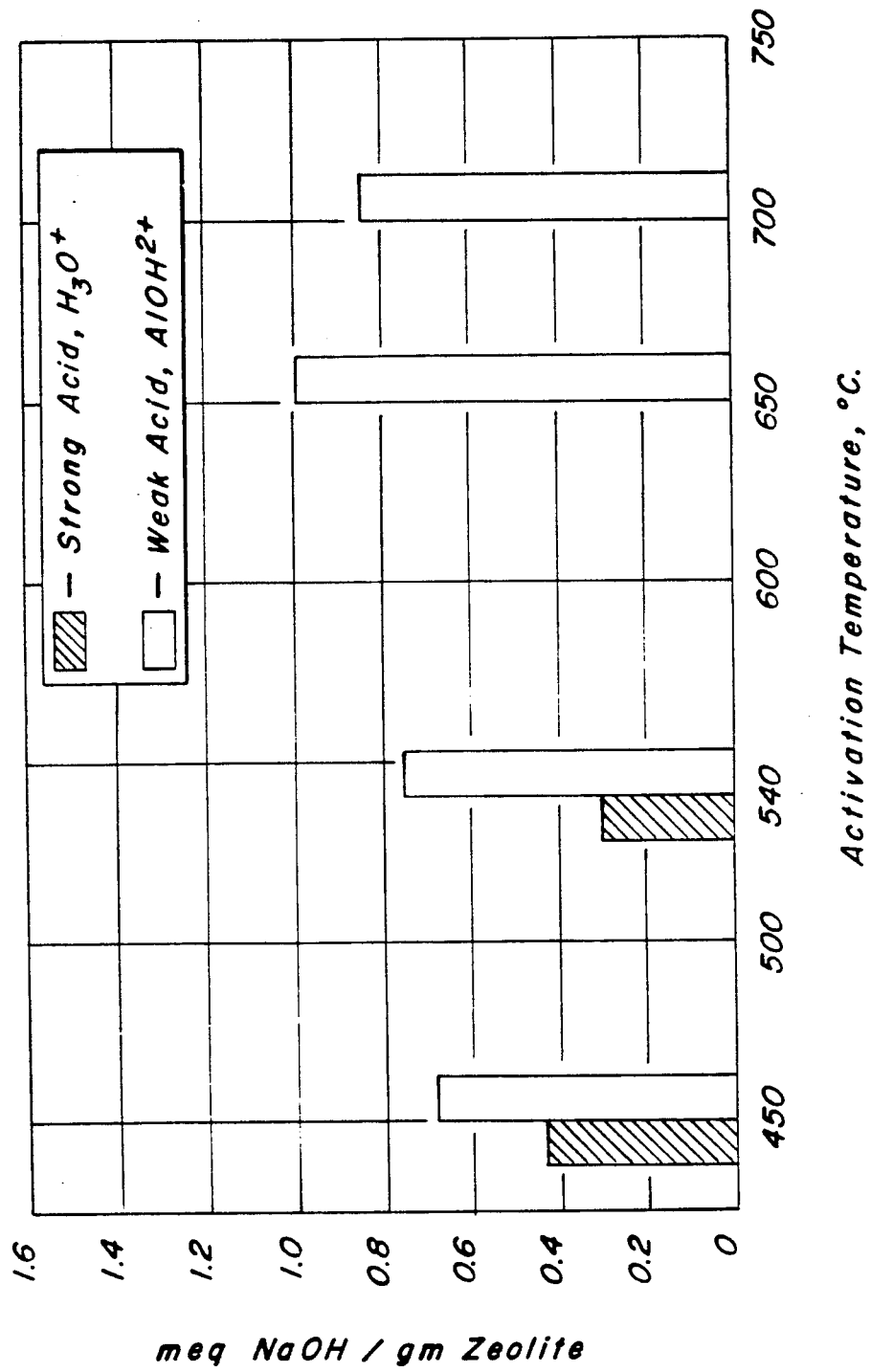

NORMAL PARAFFIN HYDROCARBON ISOMERIZATION PROCESS USING ACTIVATED ZEOLITE BETA

CROSS-REFERENCE TO RELATED APPLICATIONS

The present application is a continuation-in-part of copending U.S. Ser. No. 366,263, filed June 12, 1989, and now abandoned, which is a division of U.S. Ser. No. 175,332, filed on Mar. 30, 1988, and now abandoned.

FIELD OF THE INVENTION

This invention relates to normal paraffin isomerization processes and to methods for enhancing at least one catalytic property of a crystalline microporous three-dimensional solid catalyst having the structure and composition of zeolite beta for use in normal paraffin isomerization processes.

BACKGROUND OF THE INVENTION

A wide variety of hydrocarbon conversion processes encountered in the petroleum refining industry are catalytic in nature and many of these processes use crystalline aluminosilicate zeolites as catalysts. Illustrative of such processes include, for example, dewaxing, hydrodewaxing, cracking, hydrocracking, alkylation, isomerization, aromatization, disproportionation and the like. Often, the products from such hydrocarbon conversion processes, or portions thereof, are admixed as blending components to form motor fuels such as gasoline.

The isomerization of low molecular weight normal paraffin hydrocarbons to non-normal paraffin hydrocarbons is a well known hydrocarbon conversion process and is described in various patents, for example, U.S. Pat. Nos. 4,210,771, issued to Holcombe, and 3,150,205, issued to Krane et al. This reaction is of importance in the petroleum industry because of the higher octane number of isoparaffin hydrocarbons compared to their normal paraffin hydrocarbon counterparts. Since gasoline blends require a distribution of boiling range materials, the isoparaffins in the $C_4$–$C_7$ range are valuable blending components which have a higher octane number than a corresponding gasoline fraction consisting of normal paraffins. A variety of catalysts have been prepared to catalyze the isomerization. For instance, Friedel-Crafts catalysts, such as aluminum chloride, are known to be isomerization catalysts. Halogenated catalysts, such as platinum supported on halogenated alumina support have also been used to isomerize hydrocarbons. In addition, crystalline aluminosilicate zeolites have been used in the isomerization of hydrocarbons. Both natural and synthetic crystalline aluminosilicates have been employed. Typically, the zeolites comprise a noble metal such as platinum or palladium. Included among these are the Type X and Type Y zeolites, ZSM-5 and ZSM-20 zeolites, mordenite, as well as zeolite beta.

U.S. Pat. No. 3,308,069 and Re. 28,341, both issued to Wadlinger et al., disclose a method for preparing zeolite beta. The patents disclose that zeolite beta is prepared from reaction mixtures containing tetraethylammonium hydroxide as the alkali and more specifically by heating in aqueous solution a mixture of the oxides or of materials whose chemical compositions can be completely represented as mixtures of the oxides $Na_2O$, $Al_2O_3$, $[(C_2H_5)_4N]_2O$, $SiO_2$ and $H_2O$ suitably at a temperture of about 75°–200° C. until crystallization occurs. The product which crystalizes from the hot reaction mixture is separated, suitably by centrifuging or filtration, washed with water and dried. The material so obtained may be calcined by heating in air or an inert atmosphere at a temperature in the approximate range of 400°–1700° F. or higher so long as the temperature is not sufficient to destroy the crystallinity.

U.S. Pat. No. 4,642,226, issued to Calvert et al., relates to a new and improved form of crystalline silicate having the structure of zeolite beta, to a new and useful improvement in synthesizing said crystalline silicate and to the use of said crystalline silicate as a catalyst for organic compound, e.g., hydrocarbon compound, conversion. The patent discloses the use of dibenzyldimethylammonium as a directing agent, i.e., templating agent, instead of tetraethylammonium hydroxide as described above. The patent further discloses that the zeolite beta can be ion-exchanged by conventional techniques with a salt solution. Following contact with the salt solution of the desired replacing cation, the zeolite is then preferably washed with water and dried at a temperature ranging from 65° to about 315° C. and thereafter may be calcined in air or other inert gas at temperatures ranging from about 200° to about 600° C., preferably from about 200° to about 550° C. for periods of time ranging from 1 to 48 hours or more to produce a catalytically active thermal decomposition product thereof. The patent discloses the use of zeolite beta in hydroisomerization of normal paraffins, when provided with a hydrogenation component, e.g., platinum.

U.S. Pat. No. 4,428,819, issued to Shu et al., discloses a process relating to the hydroisomerization of catalytically dewaxed lubricating oils using zeolite beta. The patent discloses that when the zeolites have been prepared in the presence of organic cations they are catalytically inactive, possibly because the intracrystalline free space is occupied by organic cations from the forming solution. It is further disclosed that the zeolites may be activated by heating in an inert atmosphere at 540° C. for one hour, for example, followed by base exchange with ammonium salts followed by calcination at 540° C. in air.

U.S. Pat. No. 4,554,145, issued to Rubin, discloses a method for the preparation of zeolite beta. In similar fashion to above cited U.S. Pat. No. 4,642,226, the patent discloses that the synthesized zeolite beta can be ion-exchanged with a salt and thereafter calcined in air or other inert gas at temperatures ranging from about 200°–550° C. for periods of time ranging from 1 to 48 hours or more to produce a catalytically active thermal decomposition product thereof. The patent discloses the use of zeolite beta in hydroisomerization of normal paraffins, when provided with a hydrogenation component, e.g., platinum.

U.S. Pat. No. 4,501,926, issued to LaPierre et al., discloses that petroleum distillate feedstocks may be effectively dewaxed by isomerizing the waxy paraffins without substantial cracking. The isomerization is carried out over zeolite beta as a catalyst and may be conducted either in the presence or absence of added hydrogen. The catalyst may include a hydrogenation/dehydrogenation component such as platinum or palladium in order to promote the reactions which occur. The hydrogenation/dehydrogenation component may be used in the absence of added hydrogen to promote certain hydrogenation/dehydrogenation reactions which will take place during the isomerization.

U.S. Pat. No. 4,518,485, issued to LaPierre et al., relates to a process for dewaxing a hydrocarbon feedstock with a relatively high pour point and containing paraffins selected from the group of normal paraffins and slightly branched paraffins and sulfur and nitrogen compounds which comprises subjecting said oil to hydrotreating in a hydrotreating zone operated at hydrotreating conditions sufficient to remove at least a portion of said sulfur and nitrogen compounds and subjecting said hydrotreated oil to catalytic dewaxing by contacting said oil with a catalyst comprising zeolite beta having a silica/alumina ratio of at least 30:1 and a hydrogenation component under isomerization conditions.

U.S. Pat. No. 4,554,065, issued to Albinson et al., describes a process for dewaxing a hydrocarbon feedstock with a relatively high pour point and containing paraffins selected from the group of normal paraffins and slightly branched paraffins which comprises subjecting said feedstock to catalytic dewaxing at catalytic dewaxing conditions by passing said feedstock, along with hydrogen, over a dewaxing catalyst comprising zeolite beta having a noble metal hydrogenation/dehydrogenation component to produce a partially dewaxed product and subjecting said partially dewaxed product to catalytic dewaxing at catalytic dewaxing conditions by passing said partially dewaxed product over a catalyst comprising zeolite beta having a base metal hydrogenation/dehydrogenation component to recover a substantially dewaxed product as a product of the process.

European Patent Application No. 0 159 846, European Patent Application No. 0 164 939 and European Patent Application No. 0 164 208 disclose particular preparation methods of zeolite beta and the use of zeolite beta in hydroisomerization of normal paraffins, when provided with a hydrogenation component, e.g., platinum.

U.S. Pat. No. 4,647,368, issued to McGuiness et al., describes an upgrading process for paraffinic naphthas which subjects a full range naphtha to hydrocracking over a zeolite beta hydrocracking catalyst to effect a selective partial hydrocracking in which the higher molecular weight n-paraffinic components of the naphtha are hydrocracked preferentially to the lower molecular weight components with concurrent isomerization of n-paraffins to isoparaffins, to form a hydrocracked effluent which comprises isobutane, $C_5$-$C_7$ paraffins and relatively higher boiling naphthenes and paraffins. The hydrocracked effluent is split to remove the isobutane and the $C_5$ and $C_7$ paraffins with the balance of the higher boiling components being used as a reformer feed. Removal of the $C_5$ and $C_7$ paraffins permits improved reformer operation with the production of a higher octane product. The isomerization of the paraffins which occurs in the hydrocracking step provides a $C_5$-$C_7$ paraffinic fraction which is of relatively higher octane number because of the shift to isoparaffins, permitting this component to be used as a gasoline blending component.

It can be seen from the disclosures of the above cited patents that zeolite beta has been prepared for use as a catalyst in normal paraffin isomerization processes. Accordingly, processes are sought for enhancing at least one catalytic property of zeolite beta, preferably catalytic activity and selectivity, for use in normal paraffin isomerization processes.

SUMMARY OF THE INVENTION

The present invention relates to processes for isomerizing normal paraffin hydrocarbons using a crystalline microporous three-dimensional solid catalyst having the structure and composition of zeolite beta wherein at least one catalytic property, i.e., catalytic activity or selectivity, is enhanced. In accordance with the present invention, the isomerization reaction is performed using a zeolite beta catalyst that has been activated by heating in air or an inert atmosphere at a temperature effective to substantially reduce, and preferably eliminate, the concentration of strong acid species without substantially reducing the concentration of weak acid species, both the strong acid and weak acid species being initially present on the catalyst.

In one aspect of the invention there is provided a process for the isomerization of normal paraffinic hydrocarbons to form non-normal paraffinic hydrocarbons which comprises contacting a hydrocarbon feedstock containing normal paraffins with an activated zeolite beta catalyst in a reaction zone at an isomerization temperature effective to convert at least a portion of the normal paraffins to non-normal paraffins and produce a product containing non-normal hydrocarbons wherein said zeolite beta catalyst has been activated prior to said feedstock contacting by heating an initial zeolite beta catalyst in air or an inert atmosphere at an initial temperature effective to form an initial concentration of weak acid species and strong acid species and continuing said heating at an activation temperature effective to substantially reduce the concentration of strong acid species without substantially reducing the concentration of weak acid species to form the activated zeolite beta catalyst.

In another aspect of the invention there is provided a process for isomerizing normal paraffin hydrocarbons to form non-normal paraffin hydrocarbons in the presence of an activated zeolite beta catalyst comprising: (a) heating an initial zeolite beta catalyst in air or an inert atmosphere at an initial temperature effective to form an initial concentration of weak acid species and strong acid species and continuing said heating at an activation temperature effective to substantially reduce the concentration of strong acid species without substantially reducing the concentration of weak acid species to form the activated zeolite beta catalyst; (b) passing a feedstock comprising said normal paraffin hydrocarbons and hydrogen to an isomerization zone containing said activated catalyst at an isomerization temperature at least 300° C. lower than said activation temperature and effective to convert at least a portion of said normal paraffin hydrocarbons into said non-normal paraffin hydrocarbons; and (c) withdrawing a product stream comprising said non-normal paraffin hydrocarbons.

BRIEF DESCRIPTION OF THE DRAWINGS

FIG. 2 illustrates the relationship between isomerization and yield of hexanes in a hydrocarbon conversion process using a zeolite beta catalyst that was calcined, ammonium-exchanged, platinum-exchanged and activated.

FIG. 3 illustrates the relationship between weak acid species, strong acid species and activation temperature for zeolite beta.

DETAILED DESCRIPTION OF THE INVENTION

Figure 1:
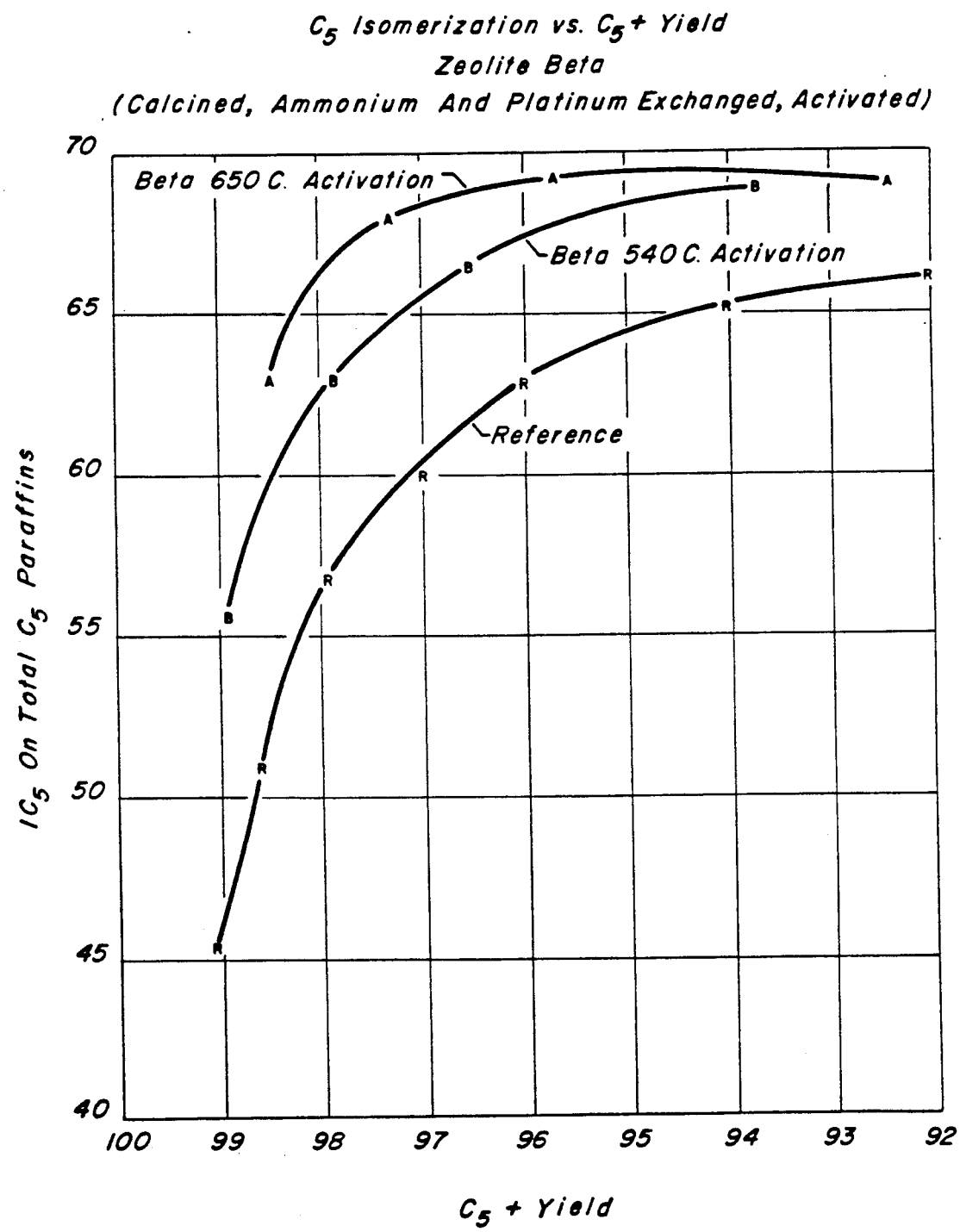
FIG. 1 illustrates the relationship between isomerization and yield of pentanes in a hydrocarbon conversion process using a zeolite beta catalyst that was calcined, ammonium-exchanged, platinum-exchanged and activated.

The crystalline microporous three-dimensional solids having the structure and composition of zeolite beta (hereinafter also denoted as "zeolite beta") employable in the catalyst compositions herein are conventional materials and are described, for example, in above-cited U.S. Pat. No. 3,308,069 and U.S. Pat. No. Re. 28,341 hereby incorporated by reference. Catalyst compositions for use in the hydrocarbon conversion processes described herein include zeolite beta generally in conjunction with at least one inorganic oxide matrix component as more fully described hereinafter.

The composition of zeolite beta in its as-synthesized form can be represented as follows:

[XNa(1.0 0.1-X)TEA]AlO$_2$YSiO$_2$ where X is less than 1, preferably less than 0.75; TEA represents the tetraethylammonium ion from the templating agent; Y is greater than 5 but less than 100. In the as-sythesized form, water of hydration may also be present in ranging amounts.

The sodium can be derived from the synthesis mixture used to prepare zeolite beta. This synthesis mixture typically contains a mixture of the oxides (or of materials whose chemical compositions can be completely represented as mixtures of the oxides) Na$_2$O, Al$_2$O$_3$, [(C$_2$H$_5$)$_4$N]$_2$O, SiO$_2$ and H$_2$O. Preferably, the mixture is held at a atemperature of about 75°-200° C. until crystallization occurs. The composition of the reaction mixture expressed in terms of mole ratios, preferably falls within the following ranges:
SiO$_2$/Al$_2$O$_3$-10 to 200;
Na$_2$O/tetraethylammonium hydroxide(TEAOH)-0.0 to 0.1;
TEAOH/SiO$_2$-0.1 to 1.0; and
H$_2$O/TEAOH - 20 to 75.

The product which crystallizes from the hot reaction mixture is separated, suitably by centrifuging or filtration, washed with water and dried.

The material so obtained should then be calcined by heating preferably in air or an inert atmosphere at a temperature usually within the range of from about 200° to about 1000° C. or higher, preferably from about 550° to about 750° C., more preferably from about 575° to about 675° C., and most preferably from about 600° to about 650° C., and for a period of time preferably in excess of 0.25 hours, more preferably in excess of 0.50 hours. The calcination should preferably not cause degradation of any catalytic sites in zeolite beta. This calcination oxidizes and/or decomposes at least a substantial portion of the catalyst templating agent, e.g., tetraethylammonium ions or dibenzyldimethylammonium ions when used instead, or in addition to TEA, from the catalyst templating agent, to hydrogen ions and removes the water to provide a zeolite beta that is substantially freed of templating agent. The calcined zeolite beta is also known as H-form zeolite beta. As used herein, the terms "at least a substantial portion" and "substantially freed" refer to at least 50 wt. %, preferably at least 75 wt. %and most preferably 100 wt. % oxidation and/or decomposition of the catalyst templating agent from the as-synthesized zeolite beta.

With 100 wt. % oxidation and/or decomposition of the catalyst templating agent, the formula of zeolite beta can then be depicted as follows:

[XNa(1.0 0.1-X)H]AlO$_2$YSiO$_2$ where X and Y are as defined above. The degree of hydration is considered to be zero following the calcination.

The H-form zeolite beta is then preferably ion-exchanged with a salt solution containing at least one hydrogen-forming cation other than hydronium, such as NH$_4$$^+$ or quaternary ammonium, in which sodium is replaced by the hydrogen-forming cation to give zeolite beta of the formula (anhydrous basis with NH$_4$$^+$ exchange):

[XNH$_4$$^+$(1 0.1-X)H]AlO$_2$YSiO$_2$ where X and Y are as defined above.

According to this invention, the hydrogen-forming cation-exchanged form of zeolite beta may optionally be subjected to metal cation-exchange to give a material of the formula (anhydrous basis):

$$\frac{X}{n} M(1\ 0.1 - X)H\ AlO_2\ YSiO_2$$

where X and Y are as described above and n is the valence of the metal M which may be any metal.

According to this invention, the hydrogen-forming cation-exchange form of zeolite beta or the metal cation-exchange form of zeolite beta can preferably be combined with at least one inorganic oxide matrix component and thereafter activated by heating in air or an inert atmosphere at a temperature and for a period of time sufficient to enhance at least one catalytic property of the catalyst in a hydrocarbon isomerization process as described hereinafter. The SiO$_2$/Al$_2$O$_3$ molar ratio of zeolite beta product employed in this invention will generally be in the range of from about 15:1 to about 45:1, preferably from about 20:1 to about 30:1; and more preferably from about 22:1 to about 26:1.

Because a templating agent such as tetraethylammonium hydroxide is used in its preparation, zeolite beta may contain occluded tetraethylammonium ions, e.g., as the hydroxide or silicate, within its pores in addition to that required by electroneutrality and indicated in the calculated formulae herein. The formulae are calculated using one equivalent of cation per aluminum atom in tetrahedral coordination in the crystal lattice.

Zeolite beta, in addition to possessing a composition as defined above, may also be characterized by its X-ray diffraction data which are set out in U.S. Pat. No. 3,308,069 and U.S. Pat. No. Re. 28,341. The significant d values (Angstroms, radiation: K alpha doublet of copper, Geiger counter spectrometer) are as shown in Table 1 below:

TABLE 1

| d Values of Reflections in Zeolite Beta |
|---|
| 11.40 + 0.2 |
| 7.40 + 0.2 |
| 6.70 + 0.2 |
| 4.25 + 0.1 |
| 3.97 + 0.1 |
| 3.00 + 0.1 |

TABLE 1-continued d Values of Reflections in Zeolite Beta 2.20 ± 0.1

As indicated above, zeolite beta is preferably ion-exchanged following calcination to remove the organic template by contacting (with or without the presence of an inorganic oxide matrix component) said zeolite beta with a salt solution of at least one hydrogen-forming cation, such as $NH_4^+$ or quaternary ammonium. Zeolite beta may optionally be metal cation-exchanged following the hydrogen-forming cation-exchange. Suitable metal cations include cations selected from the group consisting of cations of Group IIA, Group IIIA, Groups IIIB–VIIB, e.g., nickel, cobalt, iron, manganese, copper, platinum, palladium, rhodium and the like including mixtures thereof, and rare earth cations selected from cerium, lanthanum, praseodymium, neodymium, promethium, samarium, europium, gadolinium, terbium, dysprosium, holmium, erbium, thulium, ytterbium, lutetium and mixtures thereof. Of course, the metal cation present as a result of metal cation-exchange should have no substantial adverse effect on the desired hydrocarbon conversion process. As a result of such ion-exchange, the zeolite beta can contain at least one cation, e.g., hydrogen-forming cation and/or metal cation, which is different from the cations initially associated with zeolite beta as a result of its synthesis. The cation(s) present as a result of ion-exchange is preferably present in an effective amount between about 0.1 wt. % and about 20 wt. %, based on the weight of the starting zeolite beta and is typically present in an effective amount between about 0.5 wt. % and about 10 wt. %.

The ion-exchange is generally carried out by preparing a slurry of the zeolite beta catalyst by adding about 5 to 15 volumes of water per volume of catalyst, after which a solution of a selected cation is added. The ion-exchange is generally carried out at room temperature and the resulting solution is then heated to above about 50° C. and stirred at this temperature for about 0.5 to 3 hours. This mixture is then filtered and water washed to remove excess anion present as a result of the solution of the cation salt.

The zeolite beta is typically employed with at least one inorganic oxide matrix component, which combination is preferably formed after ion-exchange and prior to activation. While zeolite beta can be employed with one or more of a wide variety of inorganic oxide matrix components as hereinafter described, it is important that the pore structure of zeolite beta remain open and readily accessible to the feedstock in order to provide effective catalytic activity. Illustrative inorganic oxide matrix components which may be employed in formulating catalysts, include: amorphous catalytic inorganic oxides such as catalytically active silica/aluminas, clays, silicas, aluminas, silica-aluminas, silica-zirconias, silica-magnesias, silica-thorias, silica-berylias, silica-alumina-thorias, silica-alumina-zirconias, alumina-borias, alumina-titanias and the like and mixtures thereof. The matrix may be in the form of a sol, hydrogel or gel and is typically an alumina, silica or silica-alumina component such as a conventional silica-alumina catalyst, several types available. The matrix may itself provide a catalytic effect, such as that observed for catalytically active silica/aluminas, or it may be essentially inert. The matrix may act as a "binder" in some instances although in some instances the final catalyst may be spray dried or formed without the need of a binder.

These matrix materials may be prepared as a cogel of silica and alumina or as alumina precipitated on the preformed and preaged hydrogel. Silica may be present as a major matrix component in the solids present in the matrix, e.g., present in an amount between about 5 and about 40 wt. % and preferably between about 10 and about 30 wt. %. The silica may also be employed in the form of a cogel comprising about 75 wt. % silica and about 25 wt. % alumina or comprising about 87 wt. % silica and about 13 wt. % alumina. The inorganic oxide matrix component will typically be present in the final catalyst in an amount between about 0 and 99 wt. %, preferably between about 5 and about 90 wt. %, based on the total catalyst. It is also within the scope of the instant invention to employ other materials with the zeolite beta in the final catalysts, including clays, carbon monoxide oxidation promoters, etc.

Representative of matrix systems employable herein are disclosed in British Patent Specification No. 1,315,553, published May 2, 1973 and U.S. Pat. Nos. 3,446,727 and 4,086,187, hereby incorporated by reference.

As above-mentioned, the catalysts of the present invention may be employed with a matrix component and this may be a silica or alumina component. The alumina component may comprise discrete particles of various aluminas, e.g., pseudoboehmite. The alumina component may be in the form of discrete particles having a total surface area, as measured by the method of Brunauer, Emmett and Teller (BET), greater than about 20 square meters per gram ($M^2/g$), preferably greater than 145 $M^2/g$, for example, from about 145 to about 300 $M^2/g$. The pore volume of the alumina component will typically be greater than 0.35 cc/g. The average particle size of the alumina particles is generally less than 10 microns and preferably less than 3 microns. The alumina may be employed alone as the matrix or composited with the other matrix components.

The alumina component may be any alumina and has preferably been preformed and placed in a physical form such that its surface area and pore structure are stabilized so that when the alumina is added to an impure, inorganic gel containing considerable amount of residual soluble salts, the salts will not alter the surface and pore characteristics measurably nor will they promote chemical attack on the preformed porous alumina which could undergo change. For example, the alumina is typically an alumina which has been formed by suitable chemical reaction, the slurry aged, filtered, dried, washed free of residual salt and then heated to reduce its volatile content to less than about 15 wt. %. The alumina component may be present in the final catalyst in an amount ranging between about 5 and about 95 wt. %, preferably between about 10 and about 30 wt. % based on the total catalyst. Further, an alumina hydrosol or hydrogel or hydrous alumina slurry may be used in the catalyst preparation.

Mixtures of zeolite beta and one or more inorganic oxide matrix components may be formed into a final form for the catalyst by standard catalyst forming techniques including spray drying, pelleting, extrusion and other suitable conventional means. The use of spray drying procedures is the preferred means by which catalysts are prepared and such procedures are well known in the art. When the catalyst is formed as extruded pellets and dried in air, such are typically crushed and sized to a size less than 150 microns.

Catalysts containing zeolite beta may be prepared by any conventional method. One method of preparing such catalysts employing silica-alumina and porous alumina is to react sodium silicate with a solution of aluminum sulfate to form a silica/alumina hydrogel slurry which is then aged to give the desired pore properties, filtered to remove a considerable amount of the extraneous and undesired sodium and sulfate ions and then reslurried in water. The alumina may be prepared by reacting solutions of sodium aluminate and aluminum sulfate under suitable conditions, aging the slurry to give the desired pore properties of the alumina, filtering, drying, reslurry in water to remove sodium and sulfate ions and drying to reduce volatile matter content to less than 15 wt. %. The alumina may then be slurried in water and blended in proper amounts, with a slurry of impure silica-alumina hydrogel. The zeolite beta may then be added to this blend. A sufficient amount of each component is utilized to give the desired final composition. The resulting mixture is then filtered to remove a portion of the remaining extraneous soluble salts therefrom. The filtered mixture is then dried to produce dried solids. The dried solids are subsequently reslurried in water and washed substantially free of the undesired soluble salts. The catalyst is then dried with or without heat to a residual water content of less than about 15 wt. %. The catalyst is employed after activation as described hereinbelow.

For purposes of the present invention, the zeolite beta catalyst must be activated by heating in air or an inert atmosphere at an initial temperature effective to form an initial concentration of weak acid species and strong acid species and continuing said heating at an activation temperature effective to substantially reduce the concentration of strong acid species without substantially reducing the concentration of weak acid species, both the weak acid and strong acid species being present in the catalyst prior to the activation. Representative of the strong acid species are hydronium cations, i.e., $H_3O^+$ and representative of the weak acid species are hydroxoaluminum cations, i.e., $Al(OH)_{3-x}^{x+}$. It is not critical to the present invention how the concentration of the respective acid species is determined. One suitable procedure is set forth in the following reference; D. W. Breck and G. W. Skeels, *ZEOLITE CHEMISTRY I, THE ROLE OF ALUMINUM IN THE THERMAL TREATMENT OF AMMONIUM EXCHANGED ZEOLITE Y*, Proceedings of the Sixth International Congress on Catalysis, Vol. 2, pp. 645-659, The Chemical Society, London, (1977). This procedure generally involves treating the zeolite sample in a sodium chloride solution and then titrating the sample with sodium hydroxide to obtain two end points, one at a low pH, i.e., the strong acid, and one at a high pH, i.e., the weak acid. A result in terms of milliequivalents of sodium hydroxide per gram of zeolite can then be obtained for each acid species and translated to acid concentration.

Preferably, the activation temperature is effective to reduce the concentration of hydronium cations after activation to a level corresponding to less than 0.2 milliequivalents of NaOH per gram of zeolite beta. Even more preferably, the activation temperature is effective to substantially eliminate the hydronium cations. It is further preferred that the concentration of hydroxoaluminum cations after activation corresponds to a level of at least 0.8 milliequivalents of NaOH per gram of zeolite beta.

Many of the references hereinbefore cited disclose that the zeolite beta catalyst should be activated at a temperature of about 540° C. In accordance with the present invention, it is preferred that the activation temperature be effective to reduce the concentration of strong acid species by at least 50% as compared to the concentration of strong acid species remaining after activating at 540° C. Also, it is preferred in accordance with the present invention that the activation temperature be effective to increase the concentration of weak acid species as compared to the concentration of weak acid species remaining after activating at 540° C. More preferably, the concentration of weak acid species is increased by at least 20%. In general, the activation temperatures that correspond to the range wherein the concentration of strong acid sites can be substantially reduced without substantially reducing the concentration of weak acid sites is at least about 600° C. and less than about 700° C. Preferably, the activation temperature is from about 625°-675° C.

The activation time period is not narrowly critical and typically is in excess of 0.25 hours, preferably in excess of 0.50 hours, so long as the activation period is not sufficient to destroy the crystallinity of zeolite beta. Activation of zeolite beta catalyst for a period of about 1 hour or longer is a preferred aspect of this invention.

It is important to note that the process of the present invention can be performed on a zeolite beta-containing catalyst in any of its stages of existence beyond the as-synthesized stage. That is, the process of the present invention can be performed on zeolite beta in the as-synthesized form, calcined form or in the ion-exchanged form. Moreover, it is to be further understood that the process of the present invention can be used to treat regenerated catalysts as well, e.g., catalysts that have been subjected to oxidative regeneration for carbon removal.

Hence, in one aspect of the present invention, the calcination step can be included in the process, along with ion-exchange and activation steps described above. Thus, the present invention can be practiced on as-synthesized zeolite beta which contains templating agent by including the calcination step in the process.

In another aspect of the present invention, it is not required that the calcination step be performed. For example, a catalyst supplier may provide zeolite beta that has been previously calcined. In such a case, the process would include the ion-exchange step and the activating step as described above.

In still yet another aspect of the present invention, it is not required to perform the ion-exchange step. This would be appropriate when the zeolite beta has already been ion-exchanged as described above and perhaps dried such as when the catalyst is ready for loading in a reactor vessel.

According to a preferred aspect of this invention, a normal/non-normal paraffinic hydrocarbon feedstock is contacted with the activated zeolite beta catalyst in a reaction zone at an isomerization temperature at least 300° C. lower than the activation temperature and effective to convert at least a portion of the normal paraffin hydrocarbons into a non-normal paraffin hydrocarbon product.

The normal paraffin hydrocarbon feedstock to the reactor generally comprises normal paraffins in the $C_5$ to about $C_{15}$ carbon atom range and is preferably composed principally of the various isomeric forms of saturated hydrocarbons having from 5 to 6 carbon atoms. Such feedstocks are normally the result of refinery distillation operations, and thus may contain small amounts of $C_7$ and even higher hydrocarbons, but these are frequently present, if at all, only in trace amounts. Olefinic hydrocarbons are advantageously less than about 4 mol. % in the feedstock. Aromatic and cycloparaffin molecules have a relatively high octane number, but are to a substantial degree cracked and/or converted into molecules of much lower octane number in the isomerization process. Accordingly, the preferred feedstock should not contain more than about 25 mol. % combined aromatic and cycloparaffinic hydrocarbons. Advantageously, the $C_5$ and $C_6$ non-cyclic paraffins comprise at least 75 mol. % of the feedstock, with at least 25 mol. % being normal pentane and/or normal hexane. A feedstock of the following composition is typical:

| Components | Weight % |
|---|---|
| $C_4$ minus | 4.1 |
| $i$-$C_5$ | 24.5 |
| $n$-$C_5$ | 27.8 |
| $i$-$C_6$ | 27.4 |
| $n$-$C_6$ | 14.7 |
| $C_7$ plus | 1.5 |

In the foregoing description of the preferred feedstocks suitably treated in accordance with the present process, the expression "the various isomeric forms of pentane and hexane" is intended to denote all the branched chain and cyclic forms of the compounds, as well as the straight chain forms. Also, the prefix notations "iso" and "i" are intended to be generic designations of all branched chain and cyclic forms of the indicated compound.

The conditions at which the normal paraffin hydrocarbon isomerization process occurs can vary widely. The isomerization reaction can be conducted over a wide range of temperatures, but, in general, in the range from about 90° to about 425° C. Preferably, the isomerization temperature is between about 240°–300° C. and more preferably between about 250°–290° C. Space velocities from about 0.25 to about 5 liquid volumes per hour of isomerizable normal paraffin hydrocarbons per volume of activated zeolite beta catalyst composition are preferred with reaction zone pressures preferably within the range from about 6.9 bar (100 psi) to about 69 bar (1000 psi). It is particularly desirable to carry out the isomerization reaction in the presence of hydrogen preferably in the range from about 0.5 to about 5 moles of hydrogen per mole of isomerizable normal paraffin hydrocarbon. The function of the hydrogen is primarily to improve catalyst life, apparently by preventing polymerization of intermediate reaction products which would otherwise polymerize and deposit on the activated zeolite beta catalyst composition. It is not necessary to employ pure hydrogen since hydrogen containing gases are suitable. Product separation facilities of the isomerization process, such as catalytic conversion of naphthas, are suitable sources of hydrogen-rich gases. These hydrogen-rich gases typically contain light hydrocarbons, e.g., $C_1$–$C_3$, and may also contain other compounds.

The normal paraffin hydrocarbon conversion process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such zeolite beta catalyst compositions in series to provide for a desired product mixture. Owing to the nature of the normal paraffin hydrocarbon isomerization process, it may be desirous to carry out the certain processes by use of the zeolite beta catalyst compositions in a dynamic (e.g., fluidized or moving) bed system or any system of a variety of transport beds rather than in a fixed bed system. Such systems would readily provide for any regeneration (if required) of the zeolite beta catalyst compositions after a given period of time. If regeneration is required, the zeolite beta catalyst compositions can be continuously introduced as a moving bed to a regeneration zone where they can be regenerated, such as for example by removing carbonaceous materials by oxidation in an oxygen-containing atmosphere. In the preferred practice of some normal paraffinic hydrocarbon isomerization processes, the zeolite beta catalyst compositions will be subject to a regeneration step by burning off carbonaceous deposits accumulated during reactions.

Often, portions of the products from the isomerization process as well as other hydrocarbon conversion processes are admixed in various proportions, as blending components, as well as with other blending components to form motor fuels such as gasoline. The details of such blending operations are well known to those in the refining industry and need not be further disclosed herein.

The following examples are illustrative of this invention.

EXAMPLE 1

5.8 grams (anhydrous weight) of sodium aluminate was added to 55.6 grams of 40% tetraethylammonium hydroxide (TEAOH) in a glass beaker and stirred at room temperature for a period of five minutes. The resulting mixture was heated with stirring to reflux and held for two minutes in order to dissolve the sodium aluminate. The resulting solution was pale yellow and the sodium aluminate was incompletely dissolved. The glass beaker was transferred to a cool stirring hot plate and cooled with stirring to room temperature. As the solution cooled, additional fine solids appeared in the solution which adhered to the bottom and sides of the glass beaker. The white solid was scraped from the sides of the glass beaker with a teflon spatula and stirred. Once the sodium aluminate/TEAOH solution was cooled, 145.4 grams of Ludox LS silica was added gradually. The resulting slurry became very thick and additional hand agitation with the teflon spatula was needed to maintain the mixing of the thickening gel. The gel was mixed on the magnetic stirrer for an additional ten minutes after all the Ludox LS silica had been added. The gel was divided in half and placed in separate teflon liners of about 93 grams and 105 grams respectively. Each teflon liner was placed in a stainless steel reactor and digested in an oven at a temperature of 150° C. After six days, the two reactors were removed from the oven and cooled overnight. The contents were combined and slurried with an additional 200 milliliters of deionized water and filtered. The solid product was washed with deionized water to a pH < 10. The product was dried at room temperature and, when examined by X-ray powder diffraction, gave the characteristic X-ray powder pattern of zeolite beta. The yield of zeolite beta product was approximately 50 grams. Analyzed properties of the zeolite beta product were as follows:

| | |
|---|---|
| $Na_2O$, wt. % | 0.47 |
| $(TEA)_2O$, wt. % | 18.27 |
| $(NH_4)_2O$, wt. % | — |
| $Al_2O_3$, wt. % | 6.38 |
| $SiO_2$, wt. % | 75.27 |
| $(TEA)_2O/Al_2O_3$ | 1.18 |
| $(NH_4)_2O/Al_2O_3$ | — |
| $SiO_2/Al_2O_3$ | 20.01 |

The zeolite beta product was then calcined in flowing air at a temperature of 600° C. for a period of 2 hours to decompose the tetraethylammonium cation. After cooling, the calcined zeolite beta product was exchanged with $NH_4NO_3$ solution (5 grams $NH_4NO_3$ per gram of calcined zeolite beta product) at reflux (3 times), washed in distilled water and dried at room temperature. Analyzed properties of the calcined, ammonium-exchanged zeolite beta product were as follows:

| | |
|---|---|
| $Na_2O$, wt. % | <0.03 |
| $(TEA)_2O$, wt. % | — |
| $(NH_4)_2O$, wt. % | 2.69 |
| $Al_2O_3$, wt. % | 6.56 |
| $SiO_2$, wt. % | 89.46 |
| $(TEA)_2O/Al_2O_3$ | — |
| $(NH_4)_2O/Al_2O_3$ | 0.81 |
| $SiO_2/Al_2O_3$ | 23.15 |

EXAMPLES 2-11

The calcined, ammonium-exchanged zeolite beta product prepared in Example 1 was tested for n-butane cracking activity utilizing a cylindrical quartz tube reactor (254 millimeters in length and 10.3 millimeters internal diameter). Normal-butane cracking activity is useful screening test for catalytic activity and is indicative of isomerization activity. Separate samples of the calcined, ammoniumexchanged zeolite beta product were tested for n-butane cracking activity. The reactor was loaded with 20–40 mesh (U.S. standard) particles of the calcined, ammonium-exchanged zeolite beta product in an amount of from 0.5 to 5 grams. The calcined ammonium-exchanged zeolite beta product was then activated in the reactor for a period of 1 hour in a stream of either flowing helium or flowing air at the activation temperature indicated in Table A. below. The reaction feedstock was a helium-n-butane mixture containing 2 mol. % n-butane and, after activation of the zeolite beta product, was passed through the reactor at a rate of 50 cubic centimeters per minute with the reactor temperature maintained at 500° C. Analysis of the feedstock and the reactor effluent was carried out using conventional gas chromatography techniques. The reactor effluent was analyzed after 10 minutes of on-stream operation. From the analytical data, a pseudo-first-order rate constant (kA) was calculated.

The results are given in Table A. The lower the value of kA, the lower the catalytic activity.

TABLE A

| Example No. | Activation Temperature (°C.) | % Consumption of n-Butane | % i-Butane in Product | kA |
|---|---|---|---|---|
| 2 | 500 Air | 91.3 | 0.4 | 126 |
| 3 | 500 Helium | 88.4 | 1.1 | 128 |
| 4 | 550 Air | 89.1 | 0.2 | 132 |
| 5 | 550 Helium | — | — | — |
| 6 | 600 Air | 93.1 | 0.1 | 184 |
| 7 | 600 Helium | 93.3 | 0.1 | 170 |
| 8 | 650 Air | 98.6 | 0.0 | 245 |
| 9 | 650 Helium | 99.7 | 0.0 | 305 |
| 10 | 700 Air | 82.2 | 0.0 | 60 |
| 11 | 700 Helium | — | — | — |

EXAMPLES 12-17

In order to demonstrate improved catalytic results from high temperature activation of zeolite beta in accordance with the invention, a series of n-butane cracking tests were conducted with LZ-202 for comparison purposes. LZ-202, an omega type zeolite synthesized in an organic free system, is a known active catalyst for hydrocarbon conversion reactions. LZ-202 is available from UOP, Des Plaines, IL. Separate samples of ammonium-exchanged LZ-202 product were tested for n-butane cracking activity in accordance with the procedure described in Examples 2-11 above. The results are given in Table B below and show no unusual effect in regard to activity. Typically, a temperature of 550° C. in air is observed with most catalytic materials to be the optimum activation temperature for catalysis.

TABLE B

| Example No. | Activation Temperature (°C.) | % Consumption of n-Butane | % i-Butane in Product | kA |
|---|---|---|---|---|
| 12 | 500 Air | 76.8 | 4.1 | 71 |
| 13 | 500 Helium | 82.1 | 3.5 | 57 |
| 14 | 550 Air | 85.5 | 3.1 | 100 |
| 15 | 550 Helium | 74.1 | 4.0 | 60 |
| 16 | 600 Air | 62.5 | 4.6 | 56 |
| 17 | 600 Helium | 56.0 | 5.0 | 37 |

EXAMPLE 18

51.74 grams (anhydrous weight) of sodium aluminate were added to 361.4 grams of 40% tetraethylammonium hydroxide (TEAOH) and mixed on a magnetic stirrer for a period of five minutes at room temperature before heating to reflux. The sodium aluminate did not completely dissolve. The resulting slurry was transferred to a plastic beaker and stirred with a Heidolph mixer fitted with a jiffy pain mix stirrer until it cooled. As the slurry cooled, additional precipitate formed. When cool, 945.1 grams of Ludox LS silica were gradually added with stirring to the sodium aluminate/TEAOH slurry. A very thick gel formed and additional hand agitation was needed to keep the slurry mixing. After all the Ludox LS silica had been added, the gel was mixed for a period of five minutes and it thinned slightly. 1295.5 grams of the gel were transferred to a two liter reactor and digested for a period of seven days at a temperature of 155° C. The reactor was then cooled overnight. Initial filtration was slow, but as the product was washed with deionized water, filtration became easier. After washing until the pH of the filtrate was less than 10, the solid product was dried at room temperature and fully characterized. This preparation had a yield of 350 grams. It had the characteristic X-ray powder pattern of zeolite beta. Analyzed properties of the zeolite beta product were as follows:

| | |
|---|---|
| Na$_2$O, wt. % | 0.85 |
| (TEA)$_2$O, wt. % | 15.63 |
| (NH$_4$)$_2$O, wt. % | — |
| Al$_2$O$_3$, wt. % | 6.12 |
| SiO$_2$, wt. % | 77.40 |
| (TEA)$_2$O/Al$_2$O$_3$ | 0.94 |
| (NH$_4$)$_2$O/Al$_2$O$_3$ | — |
| SiO$_2$/Al$_2$O$_3$ | 21.44 |

The zeolite beta product was then calcined in flowing air at a temperature of 600° C. for a period of 2 hours to decompose the tetraethylammonium cation. After cooling, the calcined zeolite beta product was exchanged with NH$_4$NO$_3$ solution (5 grams NH$_4$NO$_3$ per gram of calcined zeolite beta product) at reflux (3 times), washed in distilled water and dried at room temperature. Analyzed properties of the calcined, ammonium-exchanged zeolite beta product were as follows.

| | |
|---|---|
| Na$_2$O, wt. % | <0.03 |
| (TEA)$_2$O, wt. % | — |
| (NH$_4$)$_2$O, wt. % | 2.78 |
| Al$_2$O$_3$, wt. % | 6.03 |
| SiO$_2$, wt. % | 90.26 |
| (TEA)$_2$O/Al$_2$O$_3$ | — |
| (NH$_4$)$_2$O/Al$_2$O$_3$ | 0.90 |
| SiO$_2$/Al$_2$O$_3$ | 25.39 |

EXAMPLES 19-28

Separate samples of the calcined, ammonium-exchanged zeolite beta product prepared in Example 18 were tested for n-butane cracking activity in accordance with the procedure described in Examples 2-11 above. The results are given in Table C below.

TABLE C

| Example No. | Activation Temperature (°C.) | % Consumption of n-Butane | % i-Butane in Product | kA |
|---|---|---|---|---|
| 19 | 500 Air | 87.6 | 1.7 | 139 |
| 20 | 500 Helium | 85.5 | 1.0 | 120 |
| 21 | 550 Air | 85.2 | 0.5 | 123 |
| 22 | 550 Helium | — | — | — |
| 23 | 600 Air | 95.0 | 0.0 | 182 |
| 24 | 600 Helium | 95.4 | 0.1 | 173 |
| 25 | 650 Air | 98.1 | 0.0 | 210 |
| 26 | 650 Helium | 97.6 | 0.0 | 230 |
| 27 | 700 Air | 65.1 | 0.4 | 71 |
| 28 | 700 Helium | — | — | — |

In order to demonstrate the unique nature of this invention, the following Examples 29-36 were conducted wherein the required activation step or one or more of the preferred treatment steps were omitted, i.e., calcination, and/or ion-exchange.

EXAMPLES 29-32

A zeolite beta product was prepared in accordance with the procedure described in Example 18 above except without the final activating step and without the ammonium exchange step. The zeolite beta product was tested for n-butane cracking activity in accordance with the procedure described in Examples 2-11 above. The results are given in Table D below. The results demonstrate inferior activity of this zeolite beta product in comparison with zeolite beta product prepared according to this invention and further demonstrate the importance of the required catalyst preparation step.

TABLE D

| Example No. | Calcination Temperature (°C.) | % Consumption of n-Butane | % i-Butane in Product | kA |
|---|---|---|---|---|
| 29 | 550 Air | 23.5 | 6.9 | 22 |
| 30 | 600 Air | 44.8 | 2.3 | 63 |
| 31 | 650 Air | 33.9 | 3.6 | 43 |
| 32 | 700 Air | 46.6 | 1.2 | 43 |

EXAMPLES 33

A zeolite beta product was prepared in accordance with the procedure described in Example 18 above except without the initial calcination step to oxidize the catalyst templating agent. The zeolite beta product was ammonium-exchanged and activated at a temperature of 550° C. in air and thereafter tested for n-butane cracking activity in accordance with the procedure described in Examples 2-11 above. The results are given in Table E below. The results demonstrate inferior activity of this zeolite beta product in comparison with zeolite beta product prepared according to this invention and further demonstrate the importance of the required catalyst preparation steps.

TABLE E

| Example No. | Activation Temperature (°C.) | % Consumption of n-Butane | % i-Butane in Product | kA |
|---|---|---|---|---|
| 33 | 550 Air | 50.2 | 3.7 | 67 |

EXAMPLES 34

A zeolite beta product was prepared in accordance with the procedure described in Example 18 above except without the ammonium exchange step. Instead, the zeolite beta product was hydronium ion-exchanged after the initial calcination step. The zeolite beta product was tested for n-butane cracking activity in accordance with the procedure described in Examples 2-11 above. The results are given in Table F below. The results demonstrate that hydronium-exchanged zeolite beta results in inferior activity in comparison with ammonium-exchanged zeolite beta.

TABLE F

| Example No. | Activation Temperature (°C.) | % Consumption of n-Butane | % i-Butane in Product | kA |
|---|---|---|---|---|
| 34 | 550 Air | 3.5 | 2.1 | 4 |

EXAMPLES 35-36

A zeolite beta product was prepared in accordance with the procedure described in Example 18 above except the zeolite beta product was hydrothermally treated with steam at a temperature of 600° C. following the ammonium exchange step. The product resulting from the steaming was fully crystalline. The zeolite beta product was then activated at a temperature of 650° C. and thereafter tested for n-butane cracking activity in accordance with the procedure described in Examples 2-11 above. The results are given in Table G below. The results demonstrate that hydrothermal steam calcination or activation of zeolite beta product results in inferior activity in comparison with thermal calcination or activation by heating in air or an inert atmosphere.

TABLE G

| Example No. | Activation Temperature (°C.) | % Consumption of n-Butane | % i-Butane in Product | kA |
|---|---|---|---|---|
| 35 | 650 Helium | 2.8 | 21.1 | 2 |
| 36 | 650 Helium | 5.1 | 18.8 | 3 |

EXAMPLE 37

100 grams of calcined, ammonium-exchanged zeolite beta product prepared as in Example 18 were slurried in a beaker in one liter of distilled water. A second solution containing 0.60 grams of $Pt(NH_3)_4Cl_2$ dissolved in 500 milliliters of distilled water was then added to the zeolite slurry and the zeolite beta was platinum-exchanged. The resulting slurry was then filtered and washed with distilled water, dried, extruded with peptized alumina binder and dried again for a period of sixteen hours. The extrudates contained 0.32 wt % platinum. The extrudates were split into two batches, one batch was calcined in air at a maximum temperature of 650° C. (hereinafter Catalyst A) and the second batch was calcined in air at a maximum temperature of 540° C. (hereinafter Catalyst B).

EXAMPLE 38

Separate samples of Catalyst A and Catalyst B prepared in Example 37 above were evaluated for $C_5/C_6$ isomerization activity using a fixed bed microreactor unit comprising a stainless steel tube ($\frac{3}{8}$-inch internal diameter). About 8.0 to 12.0 grams of selected Catalyst A or Catalyst B (40×60 mesh, U.S. Standard) were loaded in the microreactor and reduced under a flow of hydrogen gas at a temperature of greater than 200° C. for a period of sixteen hours. A feed consisting of 60 wt. % n-$C_5$, 35 wt. % n-$C_6$ and 5 wt. % cyclohexane was then introduced into the microreactor at a reaction pressure of 250 psig, a weight hourly space velocity (WHSV) of 1.6 hr.$^{-1}$, a hydrogen/hydrocarbon feed molar ratio of 2 and a reaction temperature specified in Table H below. Products were collected at selected run times and the products were analyzed by gas chromatography. The products were evaluated in several respects by determining:

$$i\text{-}C_5 \text{ Conversion} = \frac{i\text{-}C_5}{i\text{-}C_5 + n\text{-}C_5}$$

$$\frac{2,2\text{-}DMB(\text{Dimethylbutane})}{\text{Conversion}} = \frac{2,2\text{-}DMB}{\text{Total } C_6 \text{ Paraffins}}$$

as a means to determine the relative extent of conversion of pentane and hexane to isomeric products. The results are set forth in Table H below.

TABLE H

| Catalyst | Reaction Temperature (°C.) | i-$C_5$ Conversion | 2,2-DMB Conversion | $C_5^+$ Yield |
|---|---|---|---|---|
| A | 251.7 | 62.9 | 18.1 | 98.5 |
| A | 260.0 | 68.1 | 19.0 | 97.3 |
| A | 265.6 | 69.2 | 19.2 | 95.7 |
| A | 273.9 | 69.1 | 19.0 | 92.4 |
| B | 251.7 | 55.7 | 13.5 | 98.9 |
| B | 260.0 | 63.1 | 15.1 | 97.8 |
| B | 265.6 | 66.5 | 16.1 | 96.5 |

TABLE H-continued

| Catalyst | Reaction Temperature (°C.) | i-$C_5$ Conversion | 2,2-DMB Conversion | $C_5^+$ Yield |
|---|---|---|---|---|
| B | 273.9 | 68.9 | 18.0 | 93.7 |

The results set forth in Table H above are graphically illustrated in FIG. 1 and FIG. 2.

FIG. 1 graphically illustrates the relationship between $C_5$ isomerization conversion and $C_5^+$ yield as demonstrated by the isomerization process described in Example 39, in particular, the relationship between wt. % i-$C_5$ of total $C_5$ paraffins and the wt. % $C_5^+$ yield, utilizing a zeolite beta catalyst activated at a temperature of 650° C., a zeolite beta catalyst activated at a temperature of 540° C. and a standard reference catalyst as identified in Example 39.

FIG. 2 graphically illustrates the relationship between $C_6$ isomerization conversion and $C_5^+$ yield as demonstrated by the isomerization process described in Example 39, in particular, the relationship between wt. % 2,2-DMB (dimethylbutane) of total $C_6$ paraffins and the wt. % $C_5^+$ yield, utilizing a zeolite beta catalyst activated at a temperature of 650° C., a zeolite beta catalyst activated at a temperature of 540° C. and a standard reference catalyst as identified below.

It can be seen from FIGS. 1 and 2 that both the catalytic activity, i.e., conversion, and selectivity, i.e., yield, were substantially enhanced when the catalyst was activated at 650° C. as compared to 540° C. The delta i-$C_5$ conversion, delta 2,2-DMB conversion and delta RON (Research Octane Number) based on a standard reference catalyst were calculated at 96% $C_5^+$ yield using a 60:40 wt. % n-$C_5$:n-$C_6$ feed composition as follows:

delta i-$C_5$ Conversion=i-$C_5$ conversion-63.00 delta 2,2-DMB Conversion=2,2-DMB conversion-17.00 delta RON=0.60×0.33 (i-$C_5$ conversion-63.00)+0.40×0.65 (2,2-DMB conversion-17.00)

The standard reference catalyst was HS-10, a platinum on H-mordenite catalyst available from Shell Oil Company, La Hague, Netherlands, having an i-$C_5$ conversion of 63% and a 2,2-DMB conversion of 17%. In the formula; 0.60 and 0.40 denote the n-pentane and n-hexane composition of the feed in weight fraction, 0.33 denotes the RON octane difference between isopentane (RON=94) and normal pentane (RON=71) divided by 100, and 0.65 denotes the octane difference between 22DMB (RON=94) and n-hexane (RON=29) divided by 100. The results are set forth in Table I below as follows:

TABLE I

| Catalyst | delta i-$C_5$ Conversion | delta 2-2-DMB Conversion | Delta RON |
|---|---|---|---|
| A | 6.25 | 2.25 | 1.82 |
| B | 4.40 | −0.39 | 0.80 |
| HS-10 | 0.0 | 0.0 | 0.0 |

The results from Table I show superior catalytic performance of zeolite beta activated at a temperature of 650° C. in a $C_5/C_6$ isomerization process in comparison with the catalytic performance of the same catalyst activated at a temperature of 540° C., the typical activation temperature.

EXAMPLE 39

Approximately 1 gram samples on a dry weight basis of the ammonium ion-exchanged zeolite beta, as prepared in Example 1, were activated in a shallow bed under flowing dry air for 2 hours, removed from the oven and placed in a desiccator to cool, then placed in a 50 ml solution of 3.5M NaCl solution. Potentiometric titrations were then developed with 0.1N NaOH solution. The result of the titrations shows the amount and type of acidity developed by the zeolite under the various activation conditions.

Four samples were activated at 450, 540, 650 and 700° C. and the potentiometric titrations for each sample were developed as described above. The results are plotted in FIG. 3. After 450° C. calcination, two types of acidity were determined, strong acidity from a hydrated proton, $H_3O^+$ and a weaker acid species of hydroxoaluminum cations, $Al(OH)^{2+}$. As the activation temperature was increased, the amount of strong acid decreased as the amount of the weaker acid species increased. Without being bound by any definitive theory, it can be observed that the decrease in strong acidity is accompanied by an increase in weak acidity which corresponds well with the observed isomerization activity shown in Example 38 and FIGS. 1 and 2, and also the n-butane cracking activity shown in Example 2-11. As the strong acidity ($H_3O^+$), decreases and the weak acidity increases ($Al(OH)^{2+}$), the isomerization activity increases. Enhanced isomerization activity occurs when the strong acidity is no longer observed in the titration and when the weak acidity is also at a maximum. As the weak acidity decreases with calcination above 650° C., the isomerization activity will also be expected to decrease based on the kA values for n-butane cracking, see Examples 2-11.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof. Accordingly, the Examples demonstrate various ways in which the method of the present invention can provide a zeolite beta-containing catalyst that can have at least one enhanced catalytic property, e.g., reactivity, activity or selectivity, for use in hydrocarbon isomerization processes.

We claim:

1. A process for the isomerization of normal paraffin hydrocarbons to form non-normal paraffin hydrocarbons which comprises contacting a hydrocarbon feedstock containing normal paraffins with an activated zeolite beta catalyst in a reaction zone at an isomerization temperature effective to convert at least a portion of the normal paraffins to non-normal paraffins and produce a product containing non-normal hydrocarbons wherein said zeolite beta catalyst has been activated prior to said feedstock contacting by heating an initial zeolite beta catalyst in air or an inert atmosphere at an initial temperature effective to form an initial concentration of weak acid species and strong acid species and continuing said heating at an activation temperature effective to substantially reduce the concentration of strong acid species without substantially reducing the concentration of weak acid species to form the activated zeolite beta catalyst.

2. The process of claim 1 wherein the isomerization temperature is at least 300° C. below the activation temperature.

3. The process of claim 2 wherein the activation temperature is from about 600° to 700° C.

4. The process of claim 1 wherein the activation temperature is effective to substantially eliminate the strong acid species.

5. The process of claim 1 further comprising admixing at least a portion of said product with other blending components to form a motor fuel.

6. The process of claim 1 further comprising the steps of:
   (a) calcining a crystalline microporous three-dimensional solid composition having the structure and composition of zeolite beta by heating in air or an inert atmosphere at a temperature and for a period of time sufficient to oxidize at least a substantial portion of a catalyst templating agent initially present on said composition to form a calcined catalyst, said temperature being in the range of from about 200° to about 1000° C. and said time being in excess of about 0.25 hours; and
   (b) ion-exchanging said calcined catalyst with a salt solution containing at least one hydrogen-forming cation selected from $NH_4^+$ and quaternary ammonium to form said initial catalyst.

7. A process for isomerizing normal paraffin hydrocarbons to form non-normal paraffin hydrocarbons in the presence of an activated zeolite beta catalyst comprising:
   (a) heating an initial zeolite beta catalyst in air or an inert atmosphere at an initial temperature effective to form an initial concentration of weak acid species and strong acid species and continuing said heating at an activation temperature effective to substantially reduce the concentration of strong acid species without substantially reducing the concentration of weak acid species to form the activated zeolite beta catalyst;
   (b) passing a feedstock comprising said normal paraffin hydrocarbons and hydrogen to an isomerization zone containing said activated catalyst at an isomerization temperature at least 300° C. lower than said activation temperature and effective to convert at least a portion of said normal paraffin hydrocarbons into said non-normal paraffin hydrocarbons; and
   (c) withdrawing a product stream comprising said non-normal paraffin hydrocarbons.

8. The process of claim 7 wherein the initial temperature is less than about 540° C.

9. The process of claim 8 wherein the initial temperature is not greater than about 450° C.

10. The process of claim 7 wherein the activation temperature is from about 600° to 700° C.

11. The process of claim 7 wherein the activation temperature is from about 625° to 675° C.

12. The process of claim 7 wherein the strong acid species comprise hydronium cations.

13. The process of claim 12 wherein the weak acid species comprise hydroxoaluminum cations.

14. The process of claim 13 wherein the concentration of hydronium cations after activation corresponds to less than 0.2 milliequivalents of NaOH per gram of zeolite beta.

15. The process of claim 13 wherein the activation temperature is effective to substantially eliminate the hydronium cations.

16. The process of claim 13 wherein the concentration of hydroxoaluminum cations corresponds to at least 0.8 milliequivalents of NaOH per gram of zeolite beta.

17. The process of claim 7 wherein the activation temperature is effective to reduce the concentration of strong acid species by at least 50% as compared to the concentration of strong acid species remaining after activating at 540° C.

18. The process of claim 17 wherein the activation temperature is effective to increase the concentration of weak acid species as compared to the concentration of weak acid species remaining after activating 540° C.

19. The process of claim 18 wherein the concentration of weak acid species is increased by at least 20%.

20. The process of claim 7 wherein the isomerization temperature is from about 240° to 300° C.

21. The process of claim 20 wherein the isomerization temperature is from about 250° to 290° C.

22. The process of claim 7 wherein the feedstock comprises normal pentane and normal hexane and the product stream comprises isopentane, 2,2-dimethyl butane, 2,3-dimethyl butane, 2-methylpentane and 3-methylpentane.

* * * * *